United States Patent [19]

Fischer

[11] Plant 5,099

[45] Sep. 6, 1983

[54] AFRICAN VIOLET NAMED FIRERIDER

[75] Inventor: Arnold W. Fischer, Hanover, Fed. Rep. of Germany

[73] Assignee: Pan American Plant Company, Parrish, Fla.

[21] Appl. No.: 252,837

[22] Filed: Apr. 10, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet cultivar distinguished by its very large, purple-red wine colored flowers which are produced profusely and borne in a bouquet above a bed of medium green foliage, the plant being further distinguished by its compact rosette form, rapid growth rate and its vigorous and strong growth habit.

4 Drawing Figures

BACKGROUND OF THE NEW PLANT

This new African Violet plant originated as a seedling of unknown parentage which was discovered by me at Fallbrook, Calif., in 1977 growing among a field of various African Violet varieties being maintained in greenhouse for breeding purposes. I selected this plant because of the deep purple coloring of its relatively large and profusely produced flowers and I propagated this plant at Fallbrook in 1977, by means of cuttings from the parent plant. I found the clones of this plant to have very good growth habits and the same profuse production of flowers as the parent. Subsequently, successive generations of this plant were propagated and this work demonstrated that the novel characteristics of the plant would hold true from generation to generation and appeared to be firmly fixed. This plant is now being propagated for commercial purposes at West Chicago, Ill., and at Parrish, Fla.

DESCRIPTION OF THE DRAWINGS

This new violet plant is illustrated by the accompanying drawings, of which sheet 1 is a photographic view of a potted plant in full bloom, sheet 2 is a photographic print showing a full face view of a flower of this variety which has been hand-painted to show the true flower colors, and sheets 3 and 4 are prints of machine copies of the front and back sides, respectively, of typical leaves of this plant.

DESCRIPTION OF THE NEW PLANT

The following is a detailed description of this new African Violet plant based upon observations of greenhouse grown plants at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—Saintpaulia Ionantha.
- *Commercial.*—African Violet.

Form: Compact and of rosette shape.
Growth: Strong and vigorous.

Growth rate: Rapid.
Foliage:
- *Quantity.*—Moderate with about 20 leaves.
- *Size of leaf.*—Length — From insignificant to about 75 mm. Width — From insignificant to about 67 mm.
- *Shape of leaf.*—Oval with an acute tip, slightly oblique base and repand margins.
- *Texture.*—Pubescent.
- *Appearance.*—Glossy.
- *Color.*—Upper side — 137B. Under side — 138D.
- *Ribs and veins.*—Pinnate.
- *Rachis.*—Length: From insignificant to about 75 mm.
- *Petioles.*—Length: From insignificant to about 54 mm.

THE BUD

Form: Globular.
Size: Average, with various diameters and lengths.
Opening rate: Typical violet.
Color of petals:
- *When sepals first divide.*—74D.
- *When petals begin to unfurl.*—72A.

Sepals:
- *Number.*—Five.
- *Shape.*—Lanceolate and branched.
- *Color.*—Inside — 199A. Outside — 199A.
- *Striae.*—None.

Calyx:
- *Size.*—Small.
- *Shape.*—Calyx splits to star shape.
- *Aspect.*—Hairy.

Peduncle:
- *Character.*—Erect and rigid.
- *Length.*—From insignificant to about 65 mm.
- *Aspect.*—Hairy.
- *Color.*—199B.

THE FLOWER

Blooming habit: Intermittent.
Character of flowering: Profuse.
Flower size: Large.
- *Diameter.*—About 35 to 40 mm.
- *Depth.*—Flat.

Borne: As a cyme.

Shape: Cup-shaped when bloom first opens, becoming flat as the bloom matures.

Petalage:

*Number of petals.*—Five.

Arrangement.—Sympetalous.

*Form.*—Zygomorphic-rotate with rounded apex and repand margins.

*Texture.*—Soft.

*Appearance.*—Satiny.

*Color.*—Upper side — 72A. Under side — 74D.

*Petaloids.*—Number: From 0 to a few.

Flower stem:

*Character.*—Strong and upright.

*Length.*—From insignificant to about 65 mm.

*Color.*—199B.

Persistence: The flowers do persist.

Fragrance: None.

Lasting quality: From 10 to 20 days on the plant.

REPRODUCTIVE ORGANS

Stamens:

*Anthers.*—Number: Two. Arrangement: Monadelphous. Size: About 3 mm. square. Color: Yellow.

*Filaments.*—Length: About 3 mm. Color: Yellow.

*Pollen.*—Color — Yellow.

Pistils:

*Number.*—One.

*Style.*—Length: About 7 mm. Stigma: Color — 72A.

Ovaries: Hypogynous and tomentose.

This new African Violet cultivar is distinguished by its vigorous growth and a profusion of relative large purple-red blooms which are borne in a bouquet above a relatively wide bed of medium green foliage. The flowers are neat, single and fuschia-like and have good substance and keeping quality.

I claim:

1. A new and distinct African Violet plant, substantially as herein shown and described, characterized by its profuse production of purple-red flowers of large size.

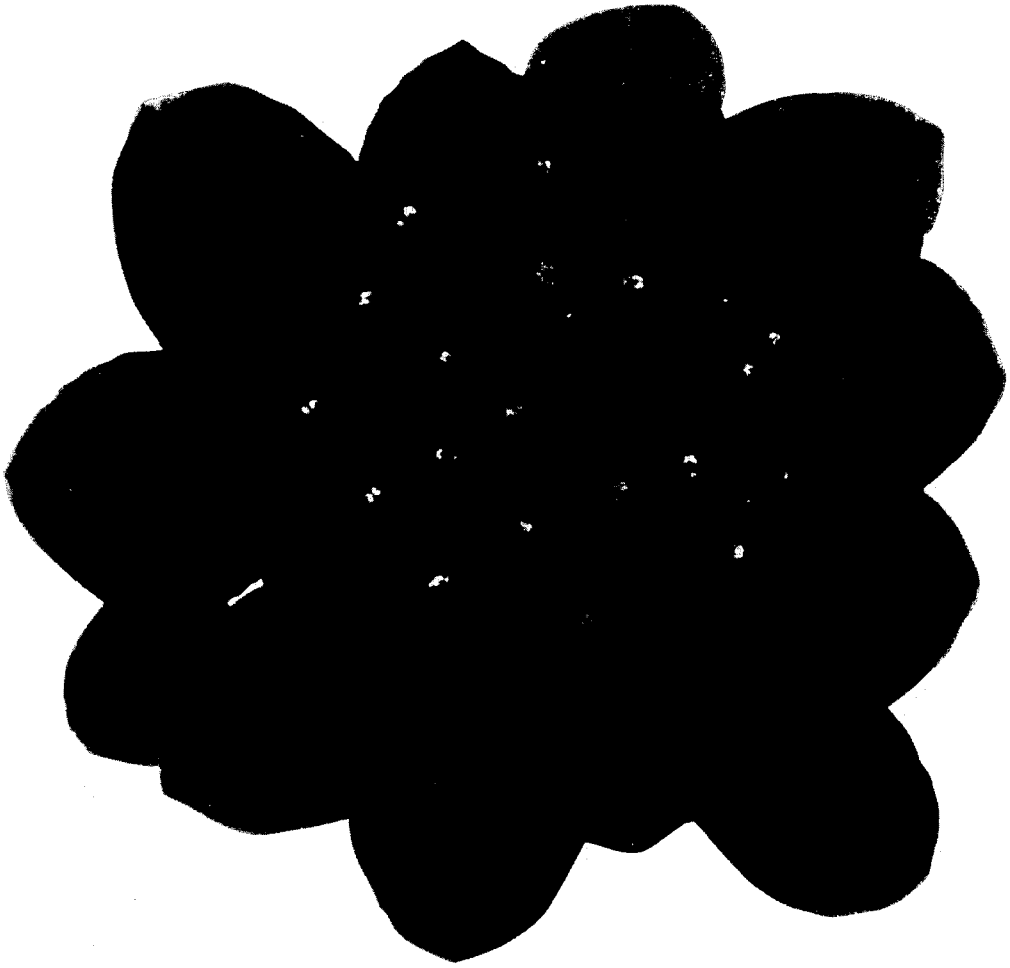

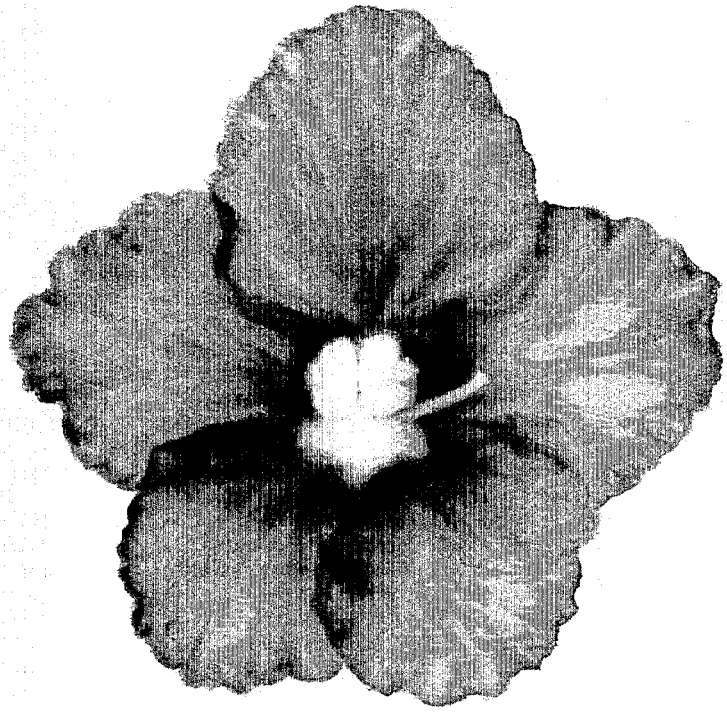

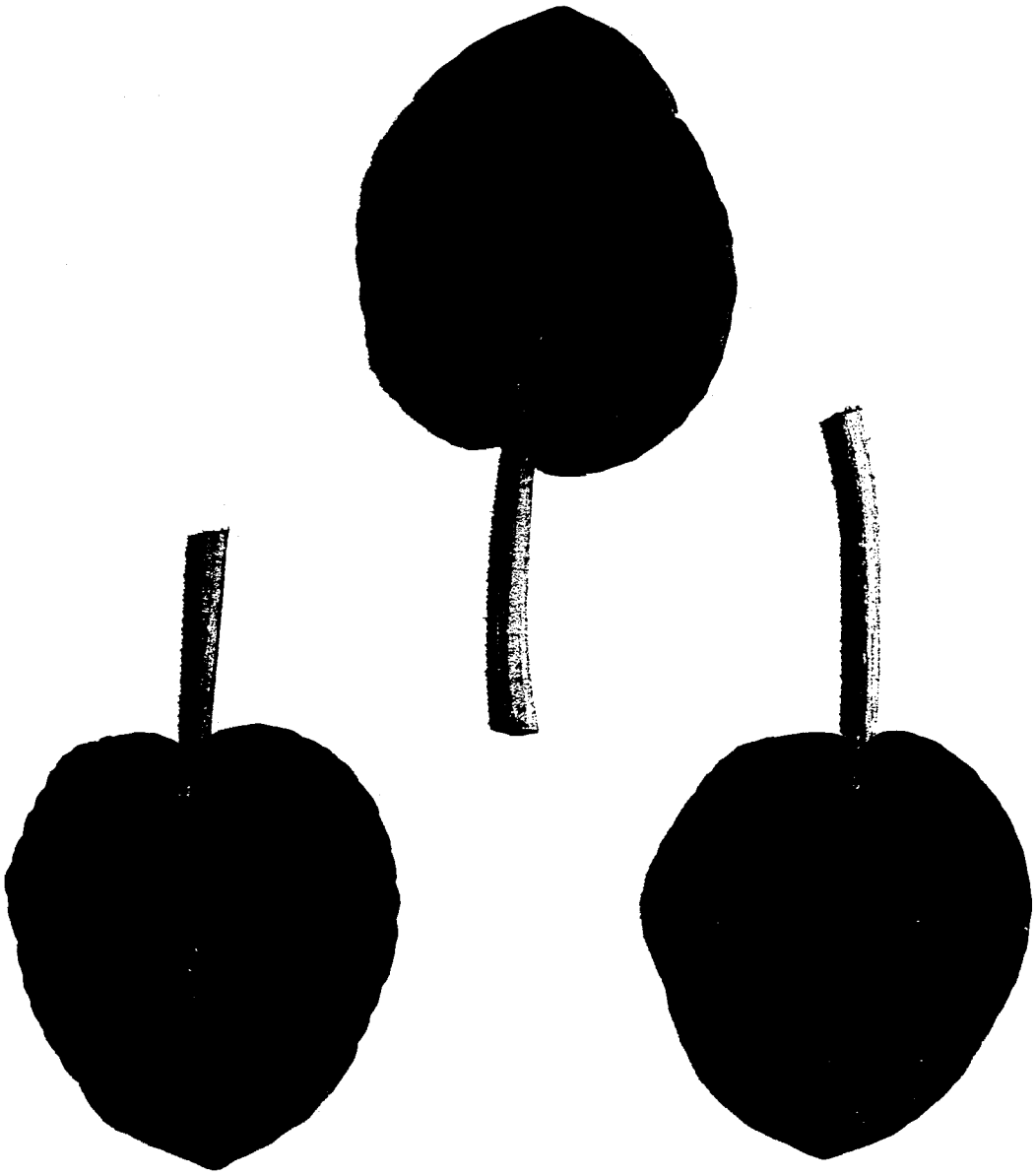

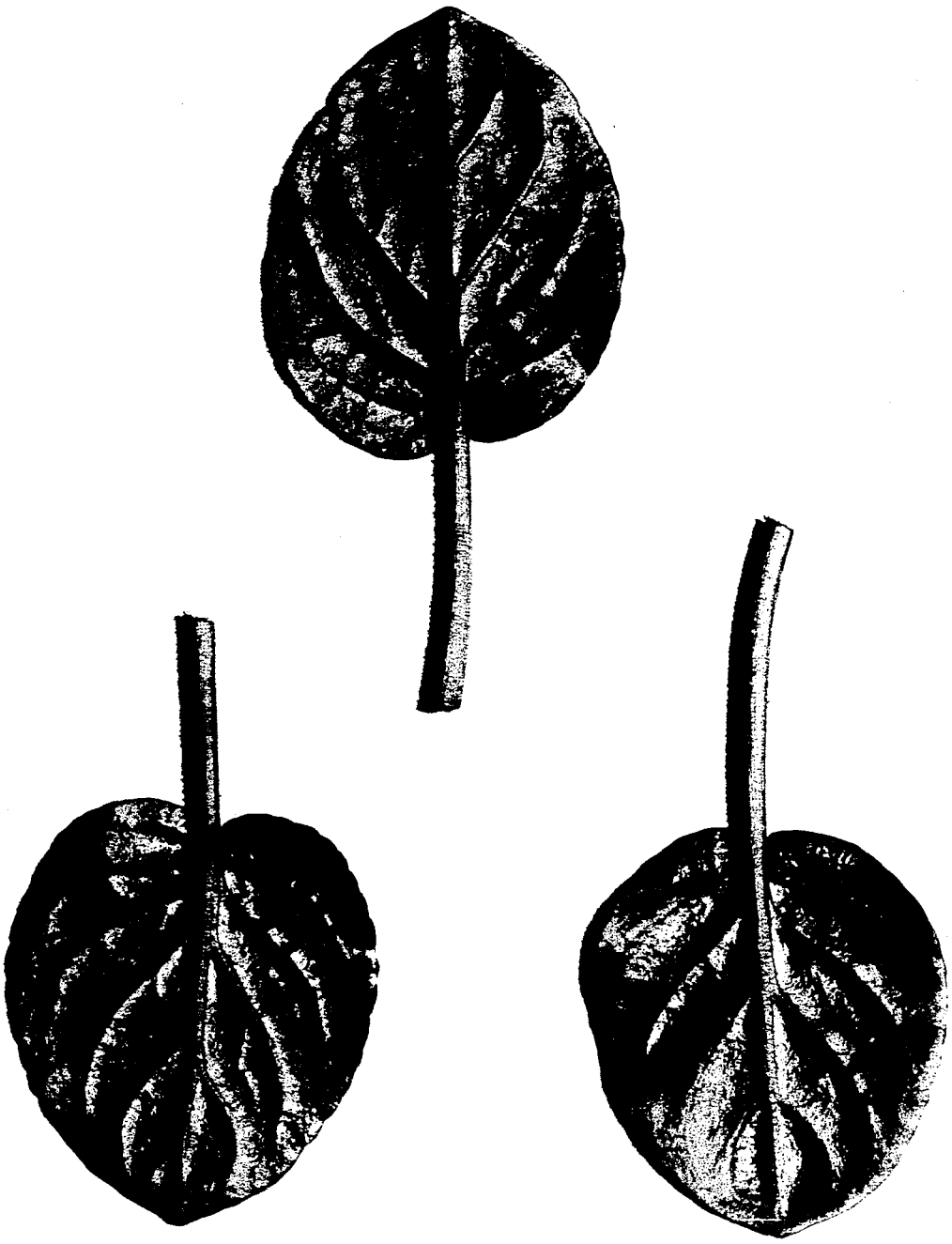

* * * * *